United States Patent
Haraldsson et al.

(10) Patent No.: US 9,476,008 B2
(45) Date of Patent: Oct. 25, 2016

(54) PROCESS FOR SEPARATING POLYUNSATURATED FATTY ACIDS FROM LONG CHAIN UNSATURATED OR LESS SATURATED FATTY ACIDS

(75) Inventors: Gudmundur G. Haraldsson, Reykjavik (IS); Bjorn Kristinsson, Kopavogur (IS)

(73) Assignee: Epax AS, Aalesund (NO)

( * ) Notice: Subject to any disclaimer, the term of this patent is extended or adjusted under 35 U.S.C. 154(b) by 625 days.

(21) Appl. No.: 13/805,102

(22) PCT Filed: Jun. 23, 2011

(86) PCT No.: PCT/IS2011/050011
§ 371 (c)(1),
(2), (4) Date: Mar. 29, 2013

(87) PCT Pub. No.: WO2011/161702
PCT Pub. Date: Dec. 29, 2011

(65) Prior Publication Data
US 2013/0196393 A1    Aug. 1, 2013

(30) Foreign Application Priority Data

Jun. 25, 2010 (IS) ............................................. 8905
Jun. 25, 2010 (IS) ............................................. 8906

(51) Int. Cl.
C12P 7/64 (2006.01)
C11B 3/00 (2006.01)
C11B 7/00 (2006.01)
C11C 3/10 (2006.01)

(52) U.S. Cl.
CPC .............. *C11B 3/003* (2013.01); *C11B 7/0075* (2013.01); *C11C 3/10* (2013.01); *C12P 7/6427* (2013.01); *C12P 7/6472* (2013.01)

(58) Field of Classification Search
None
See application file for complete search history.

(56) References Cited

FOREIGN PATENT DOCUMENTS

| CN | 101564080 A | | 10/2009 |
|---|---|---|---|
| EP | 1 300 470 A1 | | 4/2003 |
| EP | 1 411 129 A1 | | 4/2004 |
| GB | 2350610 A | * | 12/2000 |
| JP | 2000-60587 A | | 2/2000 |
| JP | 2000060587 A | * | 2/2000 |
| WO | 91/08676 A1 | | 6/1991 |
| WO | 01/05245 A1 | | 1/2001 |
| WO | 03/033633 A1 | | 4/2003 |
| WO | 2004/024930 A2 | | 5/2004 |
| WO | 2005/093027 A1 | | 10/2005 |
| WO | 2008/133573 A1 | | 11/2008 |
| WO | WO 2008133573 A1 | * | 11/2008 |

OTHER PUBLICATIONS

Haraldsson et al. (1997) J. Am Oil Chemist Society 74(11): 1419-1424.*
Breivik et al. (1997) J. Am. Oil Chemist Society 74(11): 1425-1429.*
Uhlig, Helmut. Translated and Updated by Elfriede M. Linsmaier-Bednar. (Apr. 6, 1998) Industrial Enzymes and Their Applications. John Wiley & Sons, Inc. New York. pp. 384-386.*
Cyberlipid.org. (accessed Feb. 8, 2016) Interesterification. http://www.cyberlipid.org/glycer/glyc0012.htm.*
Haraldsson et al. (1998) JAOCS 75(11): 1551-6.*
1st Technical Examination Report and Search Report for Icelandic Patent Application No. 8905, dated Nov. 5, 2010, 8 pages.
1st Technical Examination Report and Search Report for Icelandic Patent Application No. 8906, dated Nov. 5, 2010, 5 pages.
Feltes et al., "Incorporation of medium chain fatty acids into fish oil triglycerides by chemical and enzymatic interesterification," *Grasas Y Aceites* 60(2):168-176, Apr.-Jun. 2009.
Xu et al., "Purification and deodorization of structured lipids by short path distillation," *Eur. J. Lipid Sci. Technol.* 104:745-755, 2002.

* cited by examiner

Primary Examiner — Lisa J Hobbs
(74) Attorney, Agent, or Firm — Seed IP Law Group LLP

(57) ABSTRACT

A process for separating polyunsaturated fatty acids (PUFAs) such as docosahexaenoic acid (DHA) and eicosapentaenoic acid (EPA) from less saturated long chain fatty acids (LCFAs) in a lipid composition, wherein said PUFAs and LCFAs are present as (i) triglycerides, or (ii) free fatty acids or monoalkyl esters, by exchange of at least a portion of LCFAs with short and/or medium chain fatty acids (MCFAs). The process can suitably be employed on marine derived oil, marine oil 2 derived oil products and other sources of PUFAs, including PUFA-rich singe cell oils (SCOs), and oils from genetically modified organisms with a modified lipid metabolism. The inventive process is based on novel use of lipases and distillation techniques, selectively chemically modifying species in the substrate material such that the desired species and chemically similar species become sufficiently dissimilar to be separable. Thus PUFA can be effectively enriched from material such as 30 herring oil with low PUFA content and high content of equal length monounsaturated fatty acids such as 20:1 and 22:1 fatty acids.

29 Claims, No Drawings

US 9,476,008 B2

PROCESS FOR SEPARATING POLYUNSATURATED FATTY ACIDS FROM LONG CHAIN UNSATURATED OR LESS SATURATED FATTY ACIDS

FIELD OF INVENTION

The invention is in the field of lipid chemistry, in particular for industrial production of specialty lipids such as polyunsaturated fatty acid lipid concentrates for human nutritional or medical use.

TECHNICAL BACKGROUND AND PRIOR ART

Fish oils are a valuable source of n−3 polyunsaturated fatty acids (PUFAs), including docosahexaenoic acid (DHA) and eicosapentaenoic acid (EPA), which are highly beneficial for human nutrition. Extensive research has been carried out to develop and improve processes for enriching and separating such PUFAs, including lipase-based methods.

Lipases are well suited for use as catalysts in processes involving highly labile n−3 polyunsaturated fatty acids, such as EPA and DHA, occurring in marine oil. This is due to their ability to act at low temperatures, their neutral pH and their mildness in action, which helps keep to a minimum undesired side reactions such as cis-trans isomerisations, double-bond migrations, polymerisations, oxidations, etc. Thus, the utilization of lipases for the hydrolysis and various esterification and transesterification transformations of fatty acids in marine oil is already well documented.

For example, in WO 95/24459 a process is described for treating an oil composition containing triglycerides of saturated and unsaturated fatty acids to transesterification reaction conditions with ethanol in the presence of a lipase which preferentially catalyses the transesterification of the saturated and monounsaturated fatty acids, thus obtaining from marine oil sources concentrates containing more than 70% by weight of the PUFAs EPA and DHA in the form of glycerides.

WO 2004/043894 discloses a process where free fatty acids from fish oil are esterified with methanol or ethanol using a lipase that preferentially esterifies EPA over DHA to obtain a mixture from which can be separated a DHA enriched fraction, with DHA in the form of a free fatty acid, and an EPA enriched fraction, with EPA in the form of an ethyl or methyl ester.

Because of the complexity of marine raw materials, polyunsaturated fatty acid derivatives in highly purified form are not easily prepared by any single fractionation technique. Further improved methods would be appreciated to separate and purify more effectively desired PUFA components from complex lipid mixtures such as fish oils.

SUMMARY OF INVENTION

The inventors have discovered and developed a new process for efficiently separating PUFAs from long chain fatty acids that are less saturated, such as long chain saturated and monounsaturated fatty acids, including fatty acids of essentially equal or substantially similar length as the desired PUFAs. The processes of the invention can provide from oil compositions containing PUFAs—such as marine derived oil, marine oil derived oil products and other sources of PUFAs, including but not limited to PUFA-rich singe cell oils (SCOs), oils from genetically modified organisms with a modified lipid metabolism, and others—lipid concentrates enriched in PUFAs. An underlying problem which often sets practical limits on the extent to which desired components can be extracted and purified from complex natural oil sources is that together with the desired components are also components that are chemically/physically similar and therefore difficult to separate from the desired species. For example, certain abundant sources of PUFA material, such as marine oil from pelagic fish such as herring and anchovy, contain substantial amounts of monounsaturated fatty acid of same and similar length as the desired PUFAs, which are in particular DHA and EPA. If one hydrolyses such marine oil and attempts to separate out the desired PUFA fatty acids such as DHA, it turns out to be quite challenging to separate these from the similar length saturated or less unsaturated fatty acids. The inventive process is based on novel use of lipases and distillation techniques, in order to selectively chemically modify species in the raw material such that the desired species and chemically/physically similar species become sufficiently dissimilar to be separable. This is achieved in that fatty acid species that are difficult to separate from desired PUFA species are selectively modified to another form than the bulk of the PUFA material, by replacement with short and/or medium chain fatty acid species (MCFAs).

In the process, the PUFA-containing substrate material is typically provided in the form of triglycerides, as free fatty acids or in monoalkyl ester form.

Two basic pathways can be followed according to the invention, and both are described in detail and exemplified in the application. Both rest on the same underlying principle, to selectively chemically modify with lipases either of the two hard-to-separate species, either the PUFAs or the similar length less saturated fatty acids, herein referred to as LCFAs (long chain saturated and monounsaturated fatty acids). This general class may include as well in the context of the present invention more unsaturated fatty acids than monounsaturated, and generally in this context refer to long chain fatty acids other than the desired PUFAs.

According to the first primary approach, the PUFA-containing source material is provided in triglyceride form. This material is mixed with a reagent composition comprising MCFAs, in the form of monoalkyl esters or free fatty acids. This obtained mixture is brought in contact with a lipase, under conditions wherein said lipase catalyses transesterification, and the lipase catalysed reaction is allowed to proceed, exchanging acyl moieties on the PUFA-containing triglycerides with MCFA acyl moieties from the MCFA monoalkyl esters or free fatty acids. The obtained product composition comprises (i) a modified triglyceride component where in particular long chain terminal glyceride acyl chains have been exchanged for MCFA acyl chains, and (ii) monoesters or free fatty acids with fatty acids derived from the terminal positions of said reacted triglycerides.

In a second primary approach, the PUFA-containing source material is provided in the form of monoalkyl esters or free fatty acids, or converted to such form if initially in other form such as when triglycerides are as the initial starting material. The originally provided or converted free fatty acid or monoalkyl ester mixture is put in contact with a reagent composition comprising MCFAs in triglyceride form, and this mixture is, just like in the previously described approach, put in contact with a lipase, under conditions where the lipase catalyses transesterification between the PUFA fatty acids or monoalkyl esters and the MCFA-containing triglycerides, and the lipase-catalysed reaction is allowed to proceed. Under suitable conditions the catalytic reaction can be stopped when the lipase has preferentially exchanged a substantial portion of MCFAs in the triglyceride component for saturated and monounsaturated fatty acids from the monoalkyl esters/fatty acids, but leaving behind a fraction of non-reacted PUFA-monoalkyl esters/ fatty acids, thereby obtaining lipid material containing desired PUFAs but from which LCFAs have been effectively removed, thus providing a material highly suitable for PUFA enrichment by separation of small and medium species from the MCFA reagent. This is achieved by selecting a lipase which is suitably fatty acid-specific, i.e. it catalyses more rapidly the interesterification of saturated and monounsaturated fatty acid monoesters/fatty acids with the SCFA/ MCFA triglycerides than of the polyunsaturated fatty acid monoesters/fatty acids.

DETAILED DESCRIPTION

The term transesterification refers generally to the reaction of triglycerides (triacylglycerols) within or between the molecules or with other acyl donors or alcohol moieties, yielding new esters by acyl transfer of fatty acid groups. Transesterification can be classified into ester-ester interchange (inter-esterification), acidolysis and alcoholysis, depending on the nature of the substrates.

Polyunsaturated fatty acids (PUFAs) as defined herein encompass fatty acids with more than one double bond in the acyl chain. PUFAs are described with the terminology where omega refers to the terminal carbon and the term omega-3 thus refers to the first carbon-carbon double bond counting from the terminal C is at the third carbon (i.e. between the third and fourth carbon). The double bond position can also be described with the term 'n–3' ("n minus 3"), which indicates that the double bond closest to the terminal is three carbons from the end (i.e. at the "n-th minus 3" carbon). Further, when a fatty acid is identified, for instance, as C18:3, this refers to the length of the fatty acid and the overall number of double bonds, the particular term thus indicates a fatty acid having 18 carbon atoms in the chain and three double bonds.

DHA and EPA are both omega-3 or n–3 fatty acids and also described as 22:6 and 20:5 fatty acids, respectively. A full and complete description of unsaturated fatty acids also includes a reference to the cis-trans configuration of the double bonds, thus DHA and EPA are both described as all-cis.

The process of the invention is based on a series of steps in order to selectively modify enzymatically the chemical species in the initial mixture of substrate material, to be able to separate species that would otherwise be difficult to separate. As mentioned above, the starting substrate material can be provided as a monoalkyl ester mixture, as free fatty acids or as a triglyceride oil.

I. PUFA-Containing Substrate in Triglyceride Form

In the general embodiments where PUFA-containing substrate is obtained and processed in triglyceride form, the triglyceride starting material is mixed with a reagent composition comprising MCFAs in the form of monoalkyl esters or free fatty acids, such as preferably but not limited to ethyl esters. The lipase catalysed step in these embodiments will provide a modified triglyceride fraction, where in particular terminal acyl chains of the substrate triglycerides have been exchanged with acyl moieties from the reagent MCFA material. The product mixture further comprises monoalkyl esters or free fatty acids which are a mixture of remaining non-reacted MCFA material and moieties originating from the substrate triglycerides.

In these embodiments, in addition to preferably use a fatty acid-selective lipase, it is preferable to use a regiospecific lipase, i.e. a lipase that preferentially catalyses transesterification of terminal position acyl moieties in the substrate triglyceride.

A crucial part of this approach is an effective separation in step (c) of species obtained after the reaction step (b) as defined in the claims. The lipase catalysed reaction step in this approach ("PUFA-TAG approach") leaves the bulk of desired PUFA moieties on the TAG backbone, but has replaced a substantial portion of other long chain fatty acid chains initially on the TAG backbone, including monounsaturated and saturated long chain fatty acids, with short and/or medium chain fatty acids derived from the added MCFA reagent. The mixture contains some unreacted monoesters or fatty acids as well as monoesters or fatty acids of the fatty acid moieties that have been removed by transesterification of the TAG. These monoesters or fatty acids can now be separated from TAGs (i.e. from a TAG fraction including modified and unreacted TAG). Preferred methods for this step include short path vacuum distillation also referred to as molecular distillation. In this context, these terms are used interchangeable. This term generally refers to high vacuum distillation techniques configured so as to allow the desired molecules that escape from the liquid phase to preferably reach the surface of the condenser before colliding with other molecules. This technique is used in particular for sensitive substances with low volatility. Due to the sensitivity of PUFAs, distillation is preferably carried out under high vacuum, low temperature and minimal residence time.

Other separation techniques are as well within the scope of the invention, such as but not limited to supercritical fluid extraction, and chromatography techniques.

The relative amounts of the PUFA-containing triglyceride substrate and added MCFA reagent in can vary, depending on the fatty acid composition of the PUFA substrate material, the MCFA reagent and the desired enrichment. In some embodiment, the amount of MCFA component is roughly the same as the amount of PUFA substrate raw material (1:1 weight ratio). In other embodiments, the ratio of substrate to reagent is about 1:0.5, i.e. half as much of the MCFA reagent as of the PUFA substrate. In some embodiments the ratio is in the range of about 1:0.1 to 1:1, such as in the range 1:0.1 to 1:0.5, in particular, such low amount of MCFA reagent can be useful when there is continuous or stepwise removal of release fatty acid moieties (monoesters/fatty acids) that come off the MCFA triglycerides with addition of fresh batch(es) of MCFA reagent. In certain embodiments the ratio is in the range of about 1:1 to 1:0.5. In other useful embodiments, more is added of the MCFA component than of the PUFA substrate material, such as in the range of 1:1.5 to 1:3, such as about 1:2 or 1:2.5.

In cases (such as e.g. for herring oil) where the amount of long chain saturated and monounsaturated fatty acids (LCFAs) is significantly higher than the amount of desired PUFAs, two or more lipase treatments may be required, such as illustrated in Example 16.

Thus, in a preferred embodiment, lipase is removed from the reaction mixture after an initial reaction period, and the fraction comprising monoalkyl esters or free fatty acids is separated from the product residue comprising triglycerides, after which a fresh batch of MCFA reagent (monoalkyl ester or free fatty acid) is added and the reaction mixture again brought in contact with lipase (the same lipase or fresh lipase). This step can be repeated once or more often, such as one, two, three or four times.

II. PUFA-Containing Substrate in Monoalkyl Ester or Free Fatty Acid Form

In the case where the PUFA-containing starting material is processed in monoalkyl ester or free fatty acid form, the material is either obtained in such form or if obtained in triglyceride form, this raw material is first converted to a monoalkyl ester mixture or free fatty acid mixture by alcoholysis or hydrolysis, respectively. This can be done with any of several suitable methods well known to the skilled person. Conventional acid or base promoted alcoholysis/hydrolysis is used in some embodiments but lipase catalysed reaction can also be used. In preferred non-limiting embodiments, the PUFA substrate is obtained or converted to ethyl ester form.

When triglyceride material has been provided or converted to monoalkyl esters or fatty acids, this ester/fatty acid composition is mixed with a MCFA reagent in triglyceride form.

The relative amounts of the PUFA-containing substrate in monoalkyl ester or free fatty acid form and added MCFA reagent in triglyceride form can vary, depending on the fatty acid composition of the PUFA substrate material, the MCFA component and the desired enrichment. In some embodiments, the ratio of PUFA substrate and MCFA reagent is about 1:1 (weight:weight ratio). In other embodiments, the ratio can be from about 0.5:1 to 5:1, i.e. from twice the amount of MCFA reagent as of the PUFA substrate, to five times more of substrate than MCFA reagent. In some embodiments the ratio is in the range of about 0.5:1 to 2.5:1, such as in the range 0.5:1, 1:1, 1.5:1 or 2:1.

In useful embodiments undesired products are removed in stepwise fashion, i.e. by removing low boiling released acyl moieties from the MCFA TAG reagent, to minimise back-reaction. This can suitably be done by first removing the lipase, such as by filtration, then distilling off low boiling esters/free fatty acids, and adding the mixture again in contact with lipase.

The term medium chain fatty acid (MCFA) generally refers in the literature to C6-C12 fatty acids, in the context herein this term is to be understood to include as well short chain fatty acids (SCFAs) with 2 to 6 carbon atoms (C2-C6 fatty acids), and also extended to C12-C18 fatty acids.

The term short chain fatty acids (SCFAs) in context of this application refers to fatty acids with 2 to 6 carbon atoms (C2-C6 fatty acids), including acetic acid, propanoic acid (propionic acid), butanoic acid (butyric acid), 2-methylpropanoic acid (isobutyric acid), pentanoic acid (valeric acid), 3-methylbutanoic acid (isovaleric acid), and hexanoic acid (caproic acid).

Consequently, the MCFA reagent, whether in triglyceride form of alkyl ester or free fatty acid form can comprise any composition of C2-C18 fatty acids, and preferably C4-C18 fatty acids or C6-C18 fatty acids. The specific type and composition of the MCFA reagent may depend on the composition of the substrate material and which PUFA(s) are desired to enrich, and/or this may depend on suitable sources of MCFA available at a given production site. In certain embodiments the MCFA component is a vegetable oil or lipid composition derived from vegetable oil. Preferred vegetable oils include but are not limited to palm oil, palm kernel oil, coconut oil and mixtures thereof. Palm oil contains a high proportion of saturated lipid, mainly palmitic acid (C16:0) or about 44%, about 39% oleic acid (C18:1) and about 10% linoleic acid (10.5%). Palm kernel oil is even more suitable for providing the MCFA reagent for the invention, as it contains only about 2% linoleic acid and about 15% oleic acid and much higher proportion of saturated medium length fatty acids (about 82% of C12:0, C14:0, C16:0, C10:0, C8:0, C18:0). Coconut oil contains as largest component about 48% of lauric acid (12:0), and a total of about 92% saturated fatty acids.

Consequently, in some embodiments, the MCFA reagent in the invention comprises fatty acids in the range from C2 to C18, and in some embodiments in the range from C2 to C14, or preferably the range from C6-C14, or in the range C6-C16 or C6-C18. It will be appreciated that in many embodiments, the MCFA reagent contains a substantial amount of fatty acids within a range such as any of the above defined, whereas remaining fatty acids may lie outside this range, e.g. above 80% or above 90% or preferably above 95% of the MCFA reagent composition within the specified desired MCFA fatty acid range.

In some embodiments, in particular when using fish derived PUFA substrate material, it may be desired to use only fish based materials in the process, i.e. to use a MCFA reagent derived from fish based material. Thus, in these embodiments, PUFA substrate material is used in triglyceride form and the MCFA reagent material comprises light weight fractions of monoalkly ester or free fatty acids from fish based lipid sources, which can be obtained as side products from other enrichment and/or separation processes in the fish lipid industry, such as lipid material derived from DHA enrichment processes (i.e. the remaining non-DHA/low-PUFA material). An example of such material is the ethyl ester MCFA reagent used in Example 14.

The substrate material used in the process of the invention can in general comprise any of various types of raw material comprising desired polyunsaturated fatty acids (PUFAs) mixed with other fatty acids, from which it is desired to concentrate and further enrich the desired PUFAs. The substrate material can be a complex mixture such as a natural fish oil or an intermediate partially processed product. For example, the process is in certain embodiments useful for separating (enriching) DHA from EPA, or DHA and EPA from long chain monounsaturated fatty acids, depending on the specificity of the chosen lipase; thus, the process is highly useful also for lipid mixtures that are not necessarily very complex, but from which it is desired to enrich PUFAs. The process is particularly suitable for enrichment from fish oil or fish oil products but can as well be advantageously used for other complex lipid materials with PUFAs and other fatty acids. The process of the invention is further useful for single cell oils (SCOs) as further described herein.

Fish oil is the most important source of DHA and EPA. Fish oils have certain characteristic features compared to other commercial oils; a high degree of unsaturation and length of fatty acid chains, a high content of long chain omega-3 PUFAs, and a great number and variety of fatty acids present in the triglycerides. There are more than 50 different fatty acids present in a typical fish oil. They generally range from C14 to C24 and include saturated, monounsaturated, polyunsaturated, omega-3, omega-6, branched, and odd-numbered fatty acid species. Fish oils in Nature are substantially only triglycerides (triacylglycerols) but typically also contain minor amounts of mono- and diacylglycerols as well as some minor amounts of other non-triacylglycerol substances such as moisture, insoluble impurities, trace metals, oxidation products, sulphur, halogen and nitrogen compounds, sterols and organic contaminants (PCBs, dioxins, etc). The raw material used in the process of the invention is preferably refined such as to minimise or eliminate such undesirable compounds.

The European Pharmacopoeia contains monographs for different fish body oils as well as fish liver oils, including monographs for plain fish oils and omega-3 concentrates, either as TAG or ethyl esters (European Pharmacopoeia, 2005).

The oil composition which is the starting substrate material in the process of the invention can be any fish oil or mixture of fish oils, unrefined oil or refined oil, plain oil and/or oil that has been enriched with prior steps. As mentioned, the substrate material can be hydrolysed or alcoholysed from triglyceride form, in the respective relevant embodiments.

The processes of the invention can also be used for other oil compositions that contain PUFAs such as PUFA-enriched ethyl ester or free fatty acid compositions, and intermediate fractions from PUFA concentration processes. Other material for which the invention is useful include single-cell oil (SCO), which refers to oil extracted from single cell micro algae or other lipid rich microorganisms. Single cell oils are produced by use of various microorganisms, e.g. *Mortierella alpina, Crypthecodinium cohnii* and *Ulkenia* sp. With genetically modified strains, SCOs can be produced with high content of e.g. arachidonic acid (ARA, 20:4, n–6), DHA or stearidonic acid (SDA, 18:4, n–3), and/or docosapentaenoic acid, (DPA, 22:5, n–3 or n–6). The process of the present invention can advantageously be used to further enrich the desired lipids extracted from SCOs.

The process is also useful for vegetable oils, many of which include various omega-6 oils such as 18:2 and 18:3, and 18:4 omega-3 oils. Valuable oil is produced from genetically modified plants, for example oil with a high content of stearidonic acid (SDA; 18:4, n–3). The process of the invention can advantageously be used to concentrate further the SDA component from other short and long chain components.

In one embodiment of the invention, the process further includes a lipase-catalysed pre-enrichment step to provide a PUFA enriched starting substrate material. In one embodiment with such pre-step, a triglyceride oil composition is contacted with a lipase and a monohydric alcohol or water under conditions where the lipase catalyses alcoholysis or hydrolysis of the triglycerides, such that unsaturated, monounsaturated and/or diunsaturated fatty acids are preferentially cleaved off the glyceride backbone, leaving a glyceride mixture (tri-, di-, and monoglycerides) enriched in desired PUFAs. The monoesters or free fatty acids (depending on whether alcoholysis or hydrolysis is applied) are then removed, such as by distillation, and the resulting enriched triglyceride concentrate is a suitable material, for the subsequent lipase catalysed interesterification step with MCFA reagent of the claimed process. Such pre-enrichment can be useful both when the substrate is proceeded with in triglyceride form with MCFA reagent in ester or free fatty acid form and also when the PUFA substrate is hydrolysed or alcoholysed prior to MCFA interesterification. Suitable lipases for such pre-step include but are not limited to *Pseudomonas* sp. lipases and *Candida rugosa* lipase.

In a related embodiment, PUFA containing starting material is provided in the form of monoalkyl esters with longer alcohol chain moieties, such as e.g. in the range of C3-C12, such as C3, C4, C5, C6, C7 or C8, or any mixtures thereof. The monoalkyl esters are brought in contact with a lipase such as above, and ethanol, methanol, or water, such that the lipase catalyses preferential transesterification, producing ethyl or methyl esters, or hydrolysis to produce free fatty acids of those fatty acid moieties that are preferentially transesterified. These ethyl esters or free fatty acids can then be removed to provide an enriched concentrate with the unreacted desired PUFAs in the monoalkyl ester form, which is suitable for the subsequent lipase catalysed reaction.

The lipase useful in the transesterification step between the lipid composition substrate and added MCFA reagent is generally a lipase which has fatty acid selectivity, such that it shows preference for LCFAs including saturated fatty acids (SAFAs) and monounsaturated fatty acids (MUFAs) over PUFAs.

The lipase is preferably a food grade enzyme but can also in some embodiments be a technical grade enzyme.

Several lipases fulfil this condition and are consequently useful in the process. Thus, useful lipases in the invention include but are not limited to *Rhizomucor miehei* lipase (formerly named *Mucor miehei* lipase), *Aspergillus niger* lipase, *Thermomyces lanuginosus* lipase, *Pseudomonas* lipase including *Pseudomonas cepacia* lipase, *Pseudomonas fluorescens*, lipase, *Candida antarctica* lipase, *Candida rugosa* lipase (formerly referred to as *Candida cylindracea* lipase), *Geotrichum candidum* lipase, *Penicillium roguefortii* lipase, *Rhizopus delemar* lipase, and *Rhizopus oryzae* lipase.

The lipase is in some embodiments immobilised on a support material. This provides several advantages. For instance, the immobilization gives the lipases higher stability, so they last longer. It also makes recovery and reuse easier, which lowers operation costs. Also, the esterification reactions are easier to manipulate when an immobilized enzyme is involved and the lipase becomes susceptible to continuous processes which may also be vital for enzymatic industrialization processes. Sometimes, immobilization leads to improvements in the performance of enzymes. Finally, the dispersion of the lipase on the surface of the support material should ensure the exposure of the lipase to the substrates, leading to dramatic increase in activity of the enzyme per weight unit and considerable cut in dosage of enzyme and thus the cost involved.

Enzymes provided in powder form can also be used.

In some embodiments a lipase is selected that discriminates between DHA and EPA, such that in the enzyme reaction step (step (b)) the lipase will to at least some extent incorporate EPA in the triglycerides (when MCFA reagent is in triglyceride form) and preferentially leave DHA esters unreacted, thus the PUFA alkyl ester fraction separated in step (c) is in this embodiment enriched in DHA over EPA. In these embodiments the lipase is preferably selected from *Candida rugosa* lipase, *Rhizomucor miehei* lipase, *Rhizopus delemar* lipase, and *Thermomyces lanuginosus* lipase.

Such enrichment of DHA over EPA is as well applicable, when the substrate is in triglyceride form and MCFA is added as monoalkyl esters or free fatty acids; the lipase will then preferentially remove EPA from the PUFA containing triglycerides, which released EPA can be removed with other released LCFAs (sucg as 20:1 and 22:1 fatty acids).

In some embodiments of the present process, the lipase-catalysed interesterification is conducted under substantially anhydrous reaction conditions. Preferably, the total amount of water in the reaction system, from all sources including the marine oil and the lipase, should be less than 5% w/w, preferably less than 1% and more preferably less than 0.5% w/w, and most desirably between 0.01-0.25% w/w. (In a typical case the marine oil starting material will contain 0.1-0.2% w/w water, absolute ethanol used as the alcohol reagent will contain 0.2-0.5% w/w water and the lipase preparation will contain 2-2.5% w/w water.) In other embodiments, more water may be present, such as in the range 1-10 wt %, including the range 5-10 wt %. Such water content may cause some lipase-catalysed hydrolysis of monoalkyl esters and triglycerides, this makes the reaction system somewhat more complex but can still be useful, increasing water activity of the reaction system. Such water content can be generated e.g. by introduction of steam, from hydrated salts, from non-soluble resins releasing bound water.

Typically the bulk of the reaction medium consists of the substrate material itself and added MCFA reagent, i.e. the lipid composition serving as raw material and added lipid MCFA reagent comprise the medium for the reaction. However, in some embodiments, an organic solvent is used in the reaction medium. The solvent can be selected from but is not limited to one or more of ethyl acetate, hexane, and iso-octane. Preferably, an amount of the solvent is added in these embodiments, e.g. in the range of about 0.25-50 wt %, such as in the range 1-50 wt %, including the range 5-50 wt %, and the range 5-25%, and preferably the range 5-10 wt %, such as 5 wt % or 10 wt %. In other embodiments a smaller amount of organic solvent is used, such as in the range of about 0.25-5 wt % and preferably in the range 0.5-3 wt %, or the range of about 0.5-2.5 wt %, including in the range of about 1-2 wt %, such as about 1 wt % or about 2 wt %.

Other advantageous embodiments make use of supercritical carbon dioxide reaction medium.

The process of the invention can advantageously be arranged both in a batch operation or continuous flow operation, where the substrate and reagent material can be fed through a column or other arrangement with immobilised enzyme.

In a useful embodiment when MCFA reagent is added as triglycerides, monoalkyl esters or free fatty acids with the short and/or medium fatty acid chain moieties derived from the added MCFA reagent triglyceride are removed from the reaction medium which subsequently is allowed to react further. This can be done e.g. in a continuous operation system where a distillation unit is connected after a lipase reaction chamber/column, and from the distillation unit the remaining product mixture is fed back to the reactant chamber and re-circulated through the lipase chamber/column. By such separation of released MCFA moieties and recirculation, a higher enrichment of PUFAs can be obtained and/or less MCFA reagent can be used.

Such approach is also applicable when PUFA substrate is in triglyceride form and MCFA reagent is in monoalkyl ester or free fatty acid form; in this case the ester/free fatty acid is removed, this fraction can be further separated by distilling off low boiling MCFA moieties, which can be added back to the reaction mixture with substrate triglycerides, and/or fresh MCFA reagent is as well added.

As mentioned above, the process may suitably be employed on starting material provided in free fatty acid or mono alkylester form, in the general approach II (PUFA ester/free fatty acid approach). For this general approach, when the PUFA-containing starting material is initially in triglyceride form, a first step of alcoholysis or hydrolysis is employed. The alcoholysis/hydrolysis can be non-enzymatic or enzymatic. Conventional base-catalysed alcoholysis/hydrolysis is useful, employing alkoxide catalyst, such as sodium ethoxide. Enzymatic alcoholysis/hydrolysis can also be suitably used, where triglyceride starting material is put in contact with a lipase, which can be the same lipase used in the interesterification step or another lipase, and a suitable alcohol for alcoholysis, or water for hydrolysis. For enzymatic alcoholysis/hydrolysis of the triglyceride material according to the invention, fatty acid selectivity is generally not of relevance, as the triglyceride material should preferably be substantially completely converted to ester or acid form. The C1-C6 monohydric alcohol used in the alcoholysis can be but is not limited to n-hexanol, n-butanol, n-pentanol, t-butanol, methanol, ethanol, n-propanol and isopropanol, where ethanol is preferred.

Separation Step:

A crucial part of the present invention is an effective separation of species obtained after the reaction steps. When the PUFA substrate is hydrolysed/alcoholysed, the lipase catalysed reaction step leaves a proportion of desired unreacted PUFA monoesters or acids, triglycerides with both remaining MCFA side chains and side chains originating from the starting material including LCFAs. The mixture also contains esters or free fatty acids with MCFA sidechains originating from the triglyceride component, i.e. the sidechains that have been replaced. These MCFA chain fatty acids or monoesters can be separated from the remaining mixture with methods which by themselves are known in the art. Preferred methods include short path vacuum distillation also referred to as molecular distillation. In this context, these terms are used interchangeable. This term generally refers to high vacuum distillation techniques configured so as to allow the desired molecules that escape from the liquid phase to preferably reach the surface of the condenser before colliding with other molecules. This technique is used in particular for sensitive substances with low volatility. Due to the sensitivity of PUFAs, distillation is preferably carried out under high vacuum, low temperature and minimal residence time.

Different types of short path distillation systems are known to the skilled person and can be used in the invention. These include centrifugal molecular distillation (rotating disk) systems and thin film evaporators with a mechanical agitation system.

In the process of the invention, the vacuum applied in the distillation is generally in the range of about 0.001-1 mbar (0.1-100 Pa). Thus, in the separation after the reaction step, a distillation temperature in the range of about 40-120° C., such as in the range of about 60-110°, or the range 80-110° C., such as in the range of about 90-110° C., is suitable for distilling short and/or medium chain alkyl esters/fatty acids (the lower temperatures can be used if the MCFA TAG component contains very short fatty acids), subsequently, the temperature can be raised to within the range of 100-145° C., such as in the range 120-140° C., in order to distill off alkyl esters of longer fatty acids chains, including the desired polyunsaturated fatty acids, leaving behind as the residue a component comprising triglycerides that contain short and medium chain fatty acids and the fatty acids that were transferred to the glycerides by the interesterification. The actual temperatures in each distillation step will also depend on the achieved vacuum.

In the "PUFA triglyceride" approach (approach I), essentially similar distillation techniques are suitably employed, wherein first ester/free fatty acid moieties (release LCFAs and unreacted MCFA moieties are removed from the triglyceride fraction, which contains modified triglycerides. The triglycerides are then suitably hydrolysed or alcoholysed as mentioned above, to provide a mixture comprising desired PUFAs and MCFA acyl moieties, which are readily separable with the above mentioned separation techniques.

The alcoholysis (or hydrolysis) of the obtained TAG fraction can be non-enzymatic or enzymatic. Conventional base-catalysed alcoholysis is useful, employing alkoxide catalyst, such as sodium ethoxide. Enzymatic alcoholysis can also be suitably used, where TAG starting material is put in contact with a lipase, which can be the same lipase used in the transesterification step or another lipase. For enzymatic alcoholysis in this step of the process, fatty acid selectivity is not of relevance, as the TAG material should preferably be substantially completely converted to monoester form. The C1-C6 monohydric alcohol used in the alcoholysis can be but is not limited to n-hexanol, methanol, ethanol, n-propanol and isopropanol, where ethanol is preferred.

The secondary separation, that is the separation of the obtained monoalkyl esters or free fatty acids after the conversion of the obtained TAG fraction, can be performed at a lower temperature ("de-gassing"), such as in the range from about room temperature to about 120° C. when applying a vacuum pressure as mentioned above, or the range 40-100°, where an optimal value will depend on the composition of the shorter fatty acid moieties to be removed.

EXAMPLES

Example 1

PUFA Substrate in Ethyl Ester Form, Enriching DHA Over EPA

A DHA-enriched ethyl ester concentrate was used as substrate material. The ethyl ester concentrate is obtained from tuna oil which originally contained about 25% DHA and 5% EPA. The tuna oil was subjected to non-enzymatic alcoholysis with sodium ethanolate catalyst and after double distillation an ester concentrate was obtained with about 50% DHA and 10% EPA. The batch of concentrate in this Example contained 13.0% EPA and 51.7% DHA. (percentages are based on area-under-curve measurements (AUC %) from GC quantitative analysis).

The ethyl ester concentrate comprising 13.0% EPA and 51.7% DHA and coldpressed coconut oil were blended together in the ratio of 1:1 (wt/wt) to form a homogeneous and clear oily phase. The amounts were 204 g of the ethyl ester concentrate and 204 g of the coconut oil. To the oil mixture was added 10% (w/w) immobilised lipase of the lipase TLL (*Thermomyces lanuginosus* lipase; from Novozyme; the immobilised lipase product contains about 10% lipase) or 40.8 g. This reaction mixture with lipase was agitated at room temperature for 24 hrs.

After filtering the lipase off, the reaction mixture was subjected to double distillation using VTA short path distillation unit (VTA Verfahrenstechnische Anlagen GmbH, Germany). The first part of the distillation was performed at 110° C. and 0.028 mbar, in which light molecular weight fatty acid esters were removed. The residue fraction weighed 293.41 g compared to 38.5 g of the distillate.

The second distillation was performed at 135° C. and 0.001 mbar where the DHA-concentrated ethyl ester fraction was collected in the distillate. A 199.5 g residue was collected (containing triglycerides) and a distillate of 92.56 g, containing PUFA-enriched ethyl esters. The distillate fraction comprised of 7.3% EPA and 74.8% DHA with DHA in 78% overall yield (AUC %).

This example clearly demonstrates how effective the interesterification is in concentrating the long chain fatty acid DHA when starting with long chain PUFA concentrate as esters, and in this particular example the result is also a partial separation of EPA from DHA, increasing the DHA/EPA wt/wt ratio, which is 4.0 in the original PUFA ethyl ester, to a ratio of over 10.

Example 2

Different PUFA Substrates in Ethyl Ester Form, Enriching DHA Over EPA

This Example illustrates how fatty acid composition is affected in order to provide more separable species, and how DHA can be readily enriched over EPA.

Different samples of esterified oil with varying PUFA composition were obtained. Samples were mixed with refined coconut oil in a weight ratio of 1:1.10% by weight of TLL (*Thermomyces lanuginosus* lipase; from Novozyme, as in Example 1) was added. The mixture was agitated at ambient temperature for 24 hrs. The interesterified ethyl esters were separated and analyzed by standard GC method.

Table 1 shows the amount of DHA, EPA, and medium chain fatty acids (MCFA) C14 and C16 in the PUFA samples prior to mixing with coconut oil and lipase reaction and Table 2 after mixing and the interesterification reaction. After the reaction, the ratio of DHA to EPA has increased by 76-103% and the relative amount of C14 and C16 has substantially increased in all samples. This is showing that the coconut oil TAGs have contributed short and medium chain FAs, providing ethyl ester PUFA samples with higher relative amount of PUFAs as well as SCFAs and MCFAs, thus much higher amount of separable species.

TABLE 1

| PUFA sample | % EPA | % DHA | C14 | C16 | DHA/EPA |
|---|---|---|---|---|---|
| A | 45.7% | 9.4% | 0.7% | 8.4% | 0.21 |
| B | 37.0% | 25.7% | 0.0% | 1.0% | 0.69 |
| C | 37.3% | 22.7% | 0.5% | 5.8% | 0.61 |
| D | 59.9% | 18.3% | 0.0% | 1.4% | 0.31 |
| E | 13.2% | 52.8% | 0.0% | 3.3% | 4.01 |
| F | 46.6% | 24.3% | 0.0% | 1.5% | 0.52 |

TABLE 2

| sample | % EPA | % DHA | C14 | C16 | DHA/EPA | DHA/EPA increase | C14 increase | C16 increase |
|---|---|---|---|---|---|---|---|---|
| A | 34.3% | 12.5% | 12.0% | 10.6% | 0.36 | 76% | 1685% | 26.1% |
| B | 24.5% | 31.9% | 10.2% | 6.0% | 1.30 | 87% | — | 491% |
| C | 25.2% | 28.3% | 10.6% | 7.9% | 1.12 | 84% | 2211% | 37.1% |
| D | 40.4% | 23.4% | 9.8% | 5.5% | 0.58 | 90% | — | 305% |
| E | 7.3% | 59.5% | 7.7% | 4.8% | 8.16 | 103% | — | 42.6% |
| F | 30.7% | 30.2% | 9.6% | 4.9% | 0.99 | 89% | — | 232% |

Example 3

Separation of DHA-Enriched Fraction

For two of the samples in Example 2, B and F, the obtained interesterified intermediate product was separated. After the lipase was filtered away, the mixture was treated by two-step distillation as follows:
(1) Pressure 0.03 mbar and T=100° C. During this step the light molecular weight esters (MCFA, SCFA) are removed.
(2) Pressure 0.001 mbar and T=135° C. During this step the DHA enriched monoethyl ester mixture was obtained.

The results are set forth in Table 3, The increase of the DHA/EPA ratio is 55% and 72% respectively, providing ethyl ester concentrates with 36% DHA in both instances.

These results provide an example where a concentrate is obtained with a high content of both DHA and EPA and where the DHA content has been boosted significantly.

*Thermomyces lanuginosus*, Novozyme) which contains about 10% of the lipase per weight of total lipase and immobilisation carrier.

The mixture was stirred at ambient room temperature for 12 hrs. The reaction was terminated by filtrating off the lipase.

TABLE 3

| PUFA sample | DHA/EPA content of sample | | Distillate (EE) | | | Residue (TG) | | | Conversion | Recovery of EPA as EE | Recovery of DHA as EE |
|---|---|---|---|---|---|---|---|---|---|---|---|
| | % A EPA | % A DHA | g fraction | % A EPA | % A DHA | g fraction | % A EPA | % A DHA | | | |
| B | 37.0% | 25.7% | 27.01 | 33.1% | 35.6% | 47.49 | 14.0% | 4.3% | 38% | 49.6% | 82.3% |
| F | 46.6% | 24.3% | 26.86 | 39.9% | 35.8% | 45.85 | 17.7% | 3.5% | 47% | 47.2% | 85.8% |
| | | | | | | | | Average | 47% | 47.2% | 85.8% |

Example 4

Mackerel Oil as TAG Form Substrate Using Ethyl Octanoate as MCFA Reagent

To 100.0 g of Jack mackerel oil comprising 8.1% EPA and 19.5% DHA were added 100.0 g of ethyl octanoate ester and 20.0 g of TLL lipase (*Thermomyces lanuginosus* lipase; from Novozyme; the immobilised lipase product contains about 10% lipase). This mixture was agitated at room temperature for 20 hours. After filtering off the lipase the light fuel ethyl esters were removed at 110° C. and 0.035 mbar using VTA short path distillation unit (VTA Verfahrenstechnische Anlagen GmbH, Germany). The fatty acid composition of the residue turned out to be 8.2% EPA and 32.1% DHA but the distillate 6.7% EPA and 1.4% DHA. The overall recovery of the DHA turned out to be impressive 97.5%.

This Example clearly demonstrates how effective the interesterification, using low molecular weight esters, is in separating the LC PUFA of EPA and DHA when they are esterified as triglycerides.

Examples 5-12

DHA Enrichment of Different TAG Substrate Materials

In the following examples, equal amounts of a triglyceride component and either a C8 or C10 ethyl ester component are blended together (in most cases 50 g and 50 g, with the addition of 5 wt % (5 g) of immobilised lipase (TTL;

The ethyl esters were removed by short path distillation at 130° C. and 0.001 mbar pressure using a VTA short path distillation lab unit (VTA Verfahrenstechnische Anlagen GmbH, Germany).

The residual glyceride mixture was then esterified with sodium ethylate in conventional manner. The formed ethyl esters were degassed to remove the low molecular short and medium chain esters (these were distilled off), that is, the esters of the fatty acid moieties that were interesterified to the glycerol backbone.

Table 4 shows:
i. initial relative amount of DHA and EPA in the raw material oil
ii. the weight of the ethyl ester fraction (distillate) obtained after reaction step (a) and relative amounts of DHA and EPA in the fraction;
iii. the weight of the glyceride fraction (Residue) obtained after step (a) and relative amounts of DHA and EPA in the fraction;
iv. "Conversion", indicating how much of the oil in the starting material has been transesterified;
v. Relative increase in DHA amount in the obtained final enriched PUFA fraction, i.e. fraction (ii) in step (d);
vi. "Recovery of DHA", indicating the overall yield in terms of recovery of DHA through the process.

The results of the example demonstrate the applicability of the process to various differing oil material with quite different fatty acid composition, as shown by the differing amount of DHA and EPA in the starting samples. The results show very high yield in terms of DHA recovery and in all cases a significant enrichment of DHA.

TABLE 4

| Example/SAMPLE | Fatty acid composition of oil | | Distillate | | | Residue | | | Conversion | DHAf/DHAl | Recovery of DHA |
|---|---|---|---|---|---|---|---|---|---|---|---|
| | % A EPA | % A DHA | g fraction | % A EPA | % A DHA | g fraction | % A EPA | % A DHA | | | |
| 2. Single cell oil + C8 EE | 0.9% | 39.1% | 11.53 | 1.3% | 4.1% | 45.43 | 1.0% | 49.2% | 23% | 1.26 | 97.9% |
| 3. TG3000 oil + C8 EE | 19.0% | 11.7% | 16.60 | 20.3% | 2.2% | 36.29 | 18.6% | 20.4% | 49% | 1.75 | 95.3% |
| 4. TG3000 oil + C10 EE | 19.0% | 11.7% | 21.16 | 17.1% | 1.1% | 41.33 | 19.9% | 20.2% | 46% | 1.73 | 97.4% |
| 5. Herring oil + C8 EE | 6.6% | 7.5% | 27.12 | 4.6% | 0.7% | 40.00 | 8.9% | 14.3% | 52% | 1.92 | 96.8% |
| 6. Mackerel oil + C8 EE | 8.1% | 19.5% | 53.16 | 7.3% | 2.7% | 75.10 | 8.1% | 32.2% | 47% | 1.65 | 94.4% |
| 7. Fish oil + C10 EE | 7.9% | 11.3% | 22.21 | 6.1% | 0.8% | 39.22 | 12.3% | 19.4% | 45% | 1.72 | 97.9% |
| 8. Tuna oil + C10 EE | 7.4% | 27.2% | 24.45 | 7.7% | 5.2% | 37.60 | 7.4% | 44.3% | 48% | 1.63 | 92.9% |
| 9. Tuna oil + C8 EE | 7.4% | 27.2% | 104.14 | 5.8% | 3.4% | 146.04 | 6.9% | 45.7% | 47% | 1.68 | 94.9% |
| | | | | | | | | Average | 48% | 1.73 | 95.8% |

Example 13

DHA Enrichment of DHA/EPA Ethyl Ester Concentrate with Coconut Oil as MCFA Reagent 200 g of high DHA concentrate was mixed with 100 g of coconut oil and 30 g of lipase TLL. Composition of the substrate DHA concentrate was as follows:

| % EPA | % DHA | % 20:1 | % 22:1 |
|---|---|---|---|
| 10.9% | 55.7% | 1.5% | 0.8% |

The mixture was stirred at room temperature. The lipase was filtered off regularly. The filtrate was placed in a short path distillator to remove the light ethyl esters being formed during the interesterification using conditions of 85° C. and 0.002 mbar. The results were as follows:

| Time (hrs) | Residue (g) | Distilate (g) |
|---|---|---|
| 4 | 237.03 | 24.78 |
| 8 | 214.93 | 16.95 |
| 12 | 208.42 | 12.29 |
| 16 | 225.44 | 8.92 |

By removing the light fractions we were able to demonstrate that lower amount of the MCFA reagent can be used, as the equilibrium will be shifted towards the products by removal of said light fuel ethyl esters.

The residue at the 16 hrs point was further concentrated first at 100° C. followed by 140° C. using 0.002 mbar pressure in both cases. The former temperature removed the lower chain fatty acids such as C14, C16 and C18 whereas the second temperature was used to distill the DHA concentrate from the residual MCFA reagent triglyceride oil. The final DHA concentrate was 69.2 g comprising in 74% overall recovery of DHA.

| % EPA | % DHA | % 20:1 | % 22:1 |
|---|---|---|---|
| 5.7% | 75.9% | 0.8% | 0.5% |

Example 14

DHA-Rich Substrate in Triglyceride Form and MCFA Reagent in Ethyl Ester Form Jack Mackerel oil was deacidified and the resulting substrate comprised of:

| % EPA | % DHA | % 20:1 | % 22:1 |
|---|---|---|---|
| 7.8% | 18.6% | 6.6% | 3.3% |

Reaction Mixture:
250 g of Jack Mackerel oil
250 g of MCFA reagent (biofuel originated from fish oil)
50 g of lipase TLL The composition of the biofuel was typically 7% EPA, <1% DHA, 0% of 20:1 and 22:1. The amount of fatty acids with chain length C18 and shorter was in the range of 92%. The amount of C14 and C16 was 70%.

The reaction was stirred at 40° C. for 3 hours at which point the lipase was filtered off and the filtrate placed in a short path distillator at 140° C. and 0.01 mbar pressure. The process was repeated again, adding a second batch of the MCFA reagent. The final residue of the modified Jack Mackerel oil of 189 g was esterified by 2% sodium ethylate resulting in a 182 g of ethylated oil. A double distillation of this ethylated oil fraction at 103° C. and then 140° C. using 0.002 mbar pressure resulting in a yellow DHA concentrate comprising

| % EPA | % DHA | % 20:1 | % 22:1 |
|---|---|---|---|
| 12.6% | 51.3% | 3.7% | 3.2% |

With an overall recovery of DHA 72% and recovery of oil 24%.

The Example demonstrates an efficient enrichment of EPA and DHA in particular, and very good enrichment of these desired PUFA species over the equal length monounsaturated fatty acids 20:1 and 22:1.

Example 15

Comparative Test, Separation by Distillation without Lipase Treatment 250 g of Jack Mackerel oil as used in Example 14 was esterified in the same manner as in the final step of Example 14, resulting in 242 g of ethyl esters. The esters were put in a short path distillator at 0.002 mbar pressure and different temperature. At 122° C. and 43% split (distillate/feed) the resulting product DHA concentrate comprised of with an overall recovery of DHA 72% and recovery of oil 29%.

| % EPA | % DHA | % 20:1 | % 22:1 |
|---|---|---|---|
| 9.1% | 47.4% | 10.6% | 9.5% |

At 52% split (distillate/feed) the resulting in a DHA concentrate comprised of with overall recovery of DHA 64% and 24% recovery of oil.

| % EPA | % DHA | % 20:1 | % 22:1 |
|---|---|---|---|
| 7.3% | 51.7% | 9.8% | 10.8% |

The distillation product shows that DHA can be enriched, from an initial concentration of 18.6% to 51.7%, but the equal length monounsaturated fatty acid 22:1 is hard to separate from DHA and is co-enriched. The ratio of DHA over 22:1 in the initial mackerel oil substrate is 5.6 and this ratio has in fact decreased in the recovered residue, to a value of 4.8. By comparing examples 14 and 15, we note that by employing interesterification with MCFA ethyl esters of oil comprising relatively high values of the long chain monounsaturated fatty acids enable us to remove them, thus making the short path distillation for enrichment of PUFAs more efficient.

Example 16

PUFA Enrichment of Herring Oil

The example below demonstrates how the efficiency of concentrating EPA and DHA in pelagic fish such as herring can be greatly improved by using the appropriate lipase and MCFA reagent. In the herring oil and the MCFA reagent the composition of the 20:1, EPA, 22:1 and DHA was as follows:

| Type of oil/ | 20:1 | % EPA | 22:1 | % DHA |
|---|---|---|---|---|
| Herring oil | 11.9% | 7.4% | 18.1% | 8.6% |
| MCFA ethyl ester reagent | 0.0% | 6.5% | 0.0% | 0.5% |

Reaction Mixture:

Weight of herring oil: 257 g

Weight of MCFA ethyl ester reagent: 257 g

Weight of lipase TLL: 51.4 g

The mixture was stirred at 50° C. for 4 hours followed by filtering off the lipase. The resulting interesterified mixture was placed in short path distillation at 140° C. and 0.002 mbar to remove the ethyl esters. The process was repeated two more times, by adding fresh batch of MCFA reagent each time, in similar manner as described above. The results from the reaction were as follows:

| Reaction batch | g MCFA reagent | g Herring oil | g lipase TLL |
|---|---|---|---|
| 1 | 257 | 257 | 51.4 |
| 2 | 195 | — | — |
| 3 | 181 | — | — |

| Residue fraction | | | | | Distillate fraction | | | | | Recovery of FFA in residue | |
|---|---|---|---|---|---|---|---|---|---|---|---|
| Weight | 20:1 | % EPA | 22:1 | % DHA | Weight | 20:1 | % EPA | 22:1 | % DHA | DHA | EPA |
| 195.41 | 5.7% | 8.1% | 9.5% | 10.0% | 264.77 | 6.1% | 6.4% | 8.6% | 0.8% | 96.1% | 102.0% |
| 181.03 | 2.5% | 7.8% | 5.4% | 10.3% | 291.28 | 2.4% | 6.9% | 4.3% | 1.1% | 92.1% | 92.6% |
| 152.99 | 1.4% | 7.7% | 3.1% | 10.8% | 195.62 | 1.2% | 7.0% | 2.3% | 1.3% | 91.1% | 92.5% |
| | | | | | | | | | Total | 80.6% | 87.3% |

The residue fraction from last reaction batch 3 was ethylated in a standard manner with 2% sodium ethylate, followed by distilling by short path distillation apparatus at 0.002 mbar. The results were as follows:

| Residue fraction | | | | | Distillate fraction | | | | | Temp | Split |
|---|---|---|---|---|---|---|---|---|---|---|---|
| Weight | 20:1 | % EPA | 22:1 | % DHA | Weight | 20:1 | % EPA | 22:1 | % DHA | ° C. | D/feed |
| 101.68 | 2.1% | 10.9% | 4.5% | 16.1% | 46.92 | 0.0% | 1.3% | 0.0% | 0.5% | 80 | 31.6% |
| 63.54 | 3.4% | 15.3% | 7.2% | 25.1% | 84.52 | 0.0% | 2.5% | 0.0% | 1.1% | 85 | 57.1% |
| 46.68 | 4.1% | 17.4% | 9.6% | 32.3% | 101.27 | 0.5% | 3.6% | 0.0% | 1.8% | 90 | 68.4% |

The recovery of EPA and DHA was as follows:

| Temp, ° C. | % (w/w) DHA | % (w/w) EPA |
|---|---|---|
| 80 | 96.9% | 94.6% |
| 85 | 89.4% | 82.2% |
| 90 | 80.9% | 69.0% |

The results demonstrate that DHA and EPA can be efficiently enriched from herring oil, which has initial low concentrations of these PUFAs and much higher concentrations of the equal length monounsaturated fatty acids 20:1 and 22:1. The ratio of DHA to 22:1 in the herring oil is 0.48, but has increased to 3.37 in the final residue, after the three-fold reaction, which represents a seven-fold increase of the ratio.

Example 17

Comparative Example, Separation by Distillation without Lipase Treatment

Herring oil was ethylated with 2% sodium ethoxide as in the last step of Example 16 and then distilled by short path distillation apparatus at 0.002 mbar. The results from stepwise distillation (at increased temperatures, see 2nd right-hand column) were as follows:

| Residue fraction | | | | | Distillate fraction | | | | | Temp | Split |
|---|---|---|---|---|---|---|---|---|---|---|---|
| Weight | 20:1 | % EPA | 22:1 | % DHA | Weight | 20:1 | % EPA | 22:1 | % DHA | ° C. | D/feed |
| 126.56 | 12.9% | 9.0% | 23.3% | 10.9% | 32.68 | 1.7% | 2.3% | 1.0% | 1.1% | 80 | 20.5% |
| 105.41 | 14.5% | 9.9% | 26.8% | 12.5% | 53.80 | 2.6% | 3.4% | 1.6% | 1.6% | 85 | 33.8% |
| 83.39 | 15.9% | 10.0% | 32.5% | 14.8% | 74.86 | 4.8% | 4.2% | 2.7% | 1.0% | 90 | 47.3% |
| 49.68 | 14.4% | 6.8% | 45.4% | 18.5% | 108.94 | 8.7% | 7.9% | 6.0% | 4.3% | 106 | 68.7% |

The recovery of EPA and DHA in the residue was as follows:

| Temp, ° C. | % (w/w) DHA | % (w/w) EPA |
|---|---|---|
| 80° | 95.8% | 93.8% |
| 85° | 89.8% | 85.0% |
| 90° | 84.3% | 72.8% |
| 106° | 48.7% | 28.2% |

Examples 16 and 17 clearly demonstrate how efficient the interesterification of herring oil by MCFA ethyl esters enables separation of the long chain monounsaturated fatty acids 20:1 and 22:1 from the desired PUFAs, as well as making the final short path distillation more selective. Thus, a much higher concentration of EPA and DHA is obtained in Example 17 (max 25% EPA+DHA) compared to Example 16 (max 50% EPA+DHA) and the ratios of DHA to 22:1 and EPA to 20:1 change dramatically.

The invention claimed is:

1. A process for separating polyunsaturated fatty acids (PUFAs) from long chain saturated and/or monounsaturated fatty acids (LCFAs) in a lipid composition, wherein said PUFAs and LCFAs are present as (i) triglycerides, or (ii) free fatty acids or monoalkyl esters, by exchange of at least a portion of said LCFAs with medium chain fatty acids (MCFAs), said process comprising:
    (a) mixing with said lipid composition said MCFAs in a form selected from (i) monoalkyl esters or free fatty acids, in a first case wherein said PUFAs and LCFAs are in the form of triglycerides, and (ii) triglycerides, in a second case wherein said PUFAs and LCFAs are in the form of free fatty acids or monoalkyl esters, to obtain a mixture;
    (b) contacting the obtained mixture with a lipase, under conditions wherein said lipase catalyses transesterification, and allowing the catalytic reaction to proceed; and
    (c) separating the product triglyceride fraction from the product free fatty acid or monoalkyl ester fraction, retaining the portion comprising PUFAs, which in the first case (i) is the product triglyceride fraction, and in the second case (ii) is the monoalkyl ester of free fatty acid fraction.

2. The process of claim 1, wherein said lipid composition that comprises PUFAs and LCFAs is obtained or derived from material selected from the group consisting of fish oil, marine animal oil, animal fat, single cell oil, and vegetable oil.

3. The process of claim 2, wherein said lipid composition that comprises PUFAs and LCFAs is fish oil or derived from fish oil.

4. The process of claim 1, wherein said lipase is selected from the group consisting of *Rhizomucor miehei* lipase, *Thermomyces lanuginosus* lipase, *Aspergillus niger* lipase, *Pseudomonas* lipase including *Pseudomonas cepacia* lipase, *Pseudomonas fluorescens*, lipase, *Candida antarctica* lipase, *Candida rugosa* lipase, *Geotrichum candidum* lipase, *Penicillium roquefortii* lipase, *Rhizopus delemar* lipase, and *Rhizopus oryzae* lipase.

5. The process of claim 4, wherein said lipase is in a form selected from immobilised form, and powder form.

6. The process of claim 1 further comprising a step of separating said lipase from the obtained mixture after step (b).

7. The process of claim 1 wherein the reaction in step (b) is performed in a continuous flow process with immobilised enzyme.

8. The process of claim 1 wherein the separation step (c) is performed with short path distillation.

9. The process of claim 1, wherein said MCFAs in the form of (i) monoalkyl esters or free fatty acid, or (ii) triglycerides, comprise fatty acid acyl chains selected from the group consisting of saturated and unsaturated acyl chains in the range of C2-C18 and preferably in the range of C6-C14 acyl chains.

10. The process of claim 1, wherein said MCFAs in the form of (i) monoalkyl esters or free fatty acids, or (ii) triglycerides, are derived from vegetable oil, preferably from palm kernel oil and/or coconut oil.

11. The process of claim 1, wherein said lipid composition comprising PUFAs and LCFAs is in the form of triglycerides, and wherein after said separation step (c), the product triglyceride fraction is retained.

12. The process of claim 11, further comprising subjecting the retained product triglyceride fraction to hydrolysis or alcoholysis, such that the triglycerides are converted to monoesters or free fatty acids, subjecting said obtained monoesters or free fatty acids to a separation step, to obtain a fraction comprising medium chain fatty acid products and a fraction comprising long chain fatty acid products, to thereby obtain a fraction enriched in PUFAs.

13. The process of claim 12, wherein said hydrolysis or alcoholysis is catalysed with a lipase which is the same as said lipase in step (b) or a different lipase.

14. The process of claim 11, wherein said separation step for separating medium chain fatty acid products from long chain fatty acid products, is a short path vacuum distillation process.

15. The process of claim 11, wherein said MCFAs in step (a) are in the form of fatty acid monoesters comprising ester side chains comprising C1-C6 ester moieties, including methyl esters, ethyl esters, propyl esters, butyl esters, pentyl esters and hexyl esters, and preferably ethyl esters.

16. The process of claim 11, wherein the MCFA reagent is derived from fish based lipid material.

17. The process of claim 11, wherein the reaction is stepwise repeated once or more, by distilling off a fraction comprising free fatty acids and/or monoalkyl esters, and adding a fresh batch of said MCFA reagent.

18. The process of claim 11, wherein said separation step (c) is a distillation step, and serves as a stripping step, for removal of undesired low concentration species, wherein said monoalkyl esters or free fatty acids which are removed by distillation serve as stripping co-distillant.

19. The process of claim 11, wherein said separating step (c) comprising short path distillation is performed at a temperature in the range of about 100-145° C., and preferably in the range of about 120-140° C.

20. The process of claim 11, wherein said MCFA reagent is provided in a ratio to said triglyceride substrate in the range of 1:2 to 2:1 (weight:weight), and preferably in the ratio of about 1:1 (w:w).

21. The process of claim 1, wherein said lipid composition comprising PUFAs and LCFAs is in the form of monoalkyl esters or free fatty acids.

22. The process of claim 21, wherein said lipid composition comprising PUFAs and LCFAs in the form of monoalkyl esters or free fatty acids is derived from a triglyceride composition, which is alcoholysed or hydrolysed.

23. The process of claim 21, wherein said separation step (c) comprises
    (i) a first step of separating from the product mixture lower boiling monoalkyl esters or free fatty acids of short and/or medium chained fatty acids, and
    (ii) a second step of separating from the product mixture higher boiling monoalkyl esters or free fatty acids comprising desired PUFAs.

24. The process of claim 23, wherein said separation steps are enacted by short path distillation.

25. The process of claim 23, wherein in step (i) distillation is performed at a temperature in a range of about 40-120° C., and in step (ii) distillation is performed at a temperature in a range of about 100-145°.

26. The process of claim 21, wherein an amount of said MCFA reagent in triglyceride form is added in a range of about 50-250% of said substrate lipid composition.

27. The process of claim 21, wherein an amount of said MCFA reagent in triglyceride form is added in a range of about 10-100% of said substrate lipid composition.

28. The process of claim 21, wherein after the reaction step (b), low boiling monoalkyl esters or free fatty acids derived from said MCFA reagent are separated from the obtained product mixture, and the remaining product mixture is re-circulated to a further lipase catalysed reaction.

29. The process of claim 1, wherein a fatty acid selective lipase is selected to selectively enrich DHA over EPA.

* * * * *